US006953940B2

(12) United States Patent
Leighley et al.

(10) Patent No.: US 6,953,940 B2
(45) Date of Patent: Oct. 11, 2005

(54) HAND-HELD GERMICIDAL LAMP WITH SAFETY FEATURES

(75) Inventors: Kenneth C. Leighley, Stony Brook, NY (US); Richard Regan, Short Hills, NJ (US); B. William Cooper, Lloyd Harbor, NY (US)

(73) Assignee: Spectronics Corporation, Westbury, NY (US)

( * ) Notice: Subject to any disclaimer, the term of this patent is extended or adjusted under 35 U.S.C. 154(b) by 267 days.

(21) Appl. No.: 09/863,586

(22) Filed: May 16, 2001

(65) Prior Publication Data

US 2001/0042842 A1 Nov. 22, 2001

Related U.S. Application Data

(60) Provisional application No. 60/232,258, filed on Sep. 14, 2000, and provisional application No. 60/204,683, filed on May 17, 2000.

(51) Int. Cl.[7] ............................................. H01J 37/20
(52) U.S. Cl. .............................. 250/455.11; 250/504 H
(58) Field of Search ......................... 250/455.11, 287, 250/423 R, 292.1

(56) References Cited

U.S. PATENT DOCUMENTS

| 3,004,128 | A |   | 10/1961 | Mikolajeski   | 200/172    |
|-----------|---|---|---------|---------------|------------|
| 3,662,175 | A | * | 5/1972  | Davidson et al. | 250/504 R |
| 4,952,369 | A |   | 8/1990  | Belilos       | 422/24     |
| 5,029,252 | A | * | 7/1991  | Ameseder      | 250/455.11 |
| 5,144,144 | A | * | 9/1992  | Borovsky      | 250/455.11 |
| 5,523,057 | A | * | 6/1996  | Mazzilli      | 422/121    |
| 5,920,075 | A | * | 7/1999  | Whitehead     | 250/492.1  |

* cited by examiner

Primary Examiner—John R. Lee
Assistant Examiner—Phillip A Johnston
(74) Attorney, Agent, or Firm—Drinker Biddle & Reath LLP (57) ABSTRACT

A hand-held germicidal UV lamp includes housing for a UV light source and an aperture for allowing the transmission of UV light. A safety switch is provided on the housing which can be moved by an activation tool. A cover is provided over the switch having an opening for accessing the switch. The opening is sized so that a human finger cannot pass through the opening and move the switch. A light shield may be provided which surrounds the aperture and limits transmission of UV light.

24 Claims, 11 Drawing Sheets

HAND-HELD GERMICIDAL LAMP WITH SAFETY FEATURES

CROSS-REFERENCE TO RELATED APPLICATIONS

This application is related to, and claims priority filing date from, U.S. provisional patent application Ser. No. 60/204,683 filed May 17, 2000, and Ser. No. 60/232,258 filed Sep. 14, 2000.

BACKGROUND OF THE INVENTION

TECHNICAL FIELD

The invention relates to ultraviolet lamps. More particularly the invention relates to hand-held germicidal UV lamps with child safety features.

Lamps producing ultraviolet (UV) light and lamps have many different useful applications. Ultraviolet radiation in the 200–300 nanometer (nm) range is effective in killing microorganisms such as airborne and surface bacteria, viruses, yeasts and molds. A Germicidal Effectiveness Curve (based upon effect on a common bacterium) shows a peak of photic absorption by the bacterial DNA at 265 nm. There are commercially available light sources that generate UV light at the 254 nm wavelength, which is close to the effectiveness peak and well within the top range of the effectiveness curve. Such light sources are used extensively in air and water purification applications in the food and beverage industry, in medical sterilization applications, drinking water purification, and sewage treatment.

A portable lamp using the 254 nm light source can be used to sterilize pathogenic microorganisms from personal contact items such as telephone receivers and key pads; computer keyboard and computer pointer devices; ATM touch screens; desk tops and counter tops; automotive surfaces; cutting boards and kitchen utensils; glasses of clear water; keys, eyes glasses and other personal items; toilet seats and flush handles; sinks, faucet handles and knobs; children's toys and play equipment; and gym equipment.

While UV light is helpful in sterilizing surfaces, overexposure to short wave UV rays can be harmful to humans. Studies have shown ill effects of overexposure to UV rays found in solar energy. Similarly, overexposure to lamp-emitted germicidal UV radiation can cause erythema of the skin similar to sunburn, and direct exposure to the eyes can cause painful inflammation of the conjunctiva, cornea and iris, or even lasting damage. Persons working extensively with UV light generally are required to wear special goggles or be shielded by non-UV transmitting protective plate glass. While adults using germicidal lamps are generally cautious of unnecessary exposure if they are made aware of the hazard, children are at risk of exposure to UV light from playing with a hand-held UV lamp. Children's skin and eyes are particularly sensitive to UV exposure. In addition, young children are innately curious of illuminated objects, and would be prone to expose themselves to UV radiation if "playing" with a hand-held germicidal UV lamp. Therefore, while a hand-held UV germicidal lamp is a desirable consumer product, measures need to be taken to reduce the risk of accidental or uninformed exposure to UV radiation. Accordingly, there exists the need for a hand-held portable UV lamp with safety features to reduce the risk of such exposure.

There is also the need for a hand-held portable UV lamp which allows a user to observe whether the UV lamp has been powered on, without exposing the user to UV radiation.

SUMMARY OF THE INVENTION

The present invention addresses the foregoing safety problems by providing a portable hand-held lamp which incorporates features to prevent unnecessary and unintended exposure to UV radiation. The lamp further includes special switches to deter children from activating the light source, and optical shielding.

One embodiment of the lamp comprises a housing enclosing the UV light source, and has a special power switch disposed within the housing that is accessible only through a small opening. The opening is too small for a child's finger to operate the switch. A special tool is used to operate the power switch. The lamp is also equipped with a tinted UV-absorbing light shield to protect the user from UV radiation.

In another embodiment of the lamp, access to the power switch is restricted by a moveable cover. In another embodiment, the lamp has an AC/DC adapter connection compatible with standard AC/DC adapter plugs. Another embodiment incorporates the lamp with a degermination chamber.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

Figure 1:
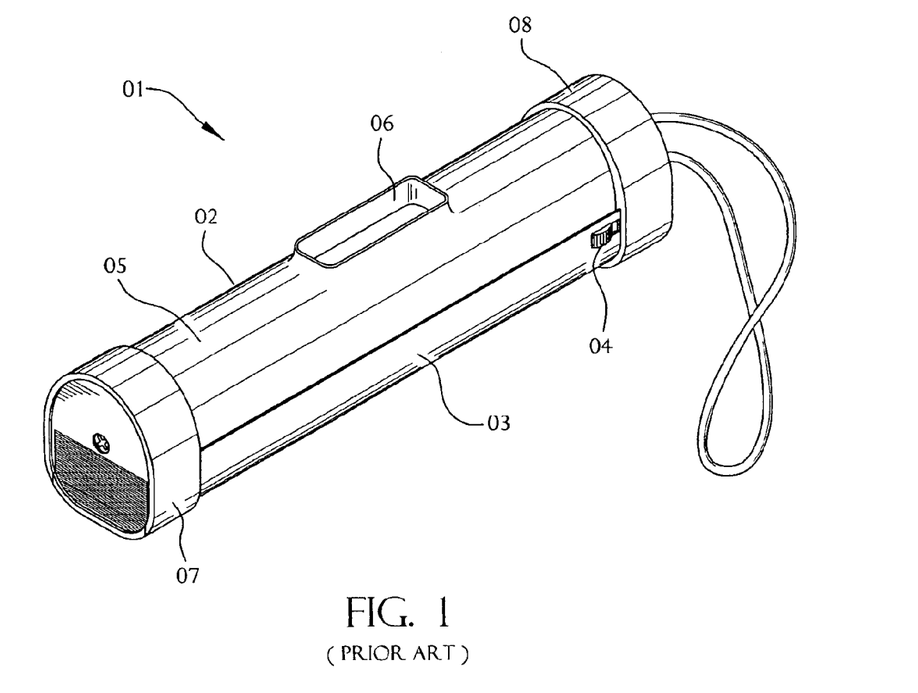
FIG. 1 is an oblique view of a commercially-available germicidal UV lamp.

FIG. 1 shows a germicidal lamp 01 of the prior art. The lamp has a housing 02 that encloses batteries and an ultraviolet (UV) light source (not visible in FIG. 1) that produces 254 nm radiation. The housing has a handle section 03 with an ON/OFF switch 04, a cover section 05 with an aperture 06 that allows light from the UV light source to exit the lamp housing, and two end caps 07, 08.

Figure 2:
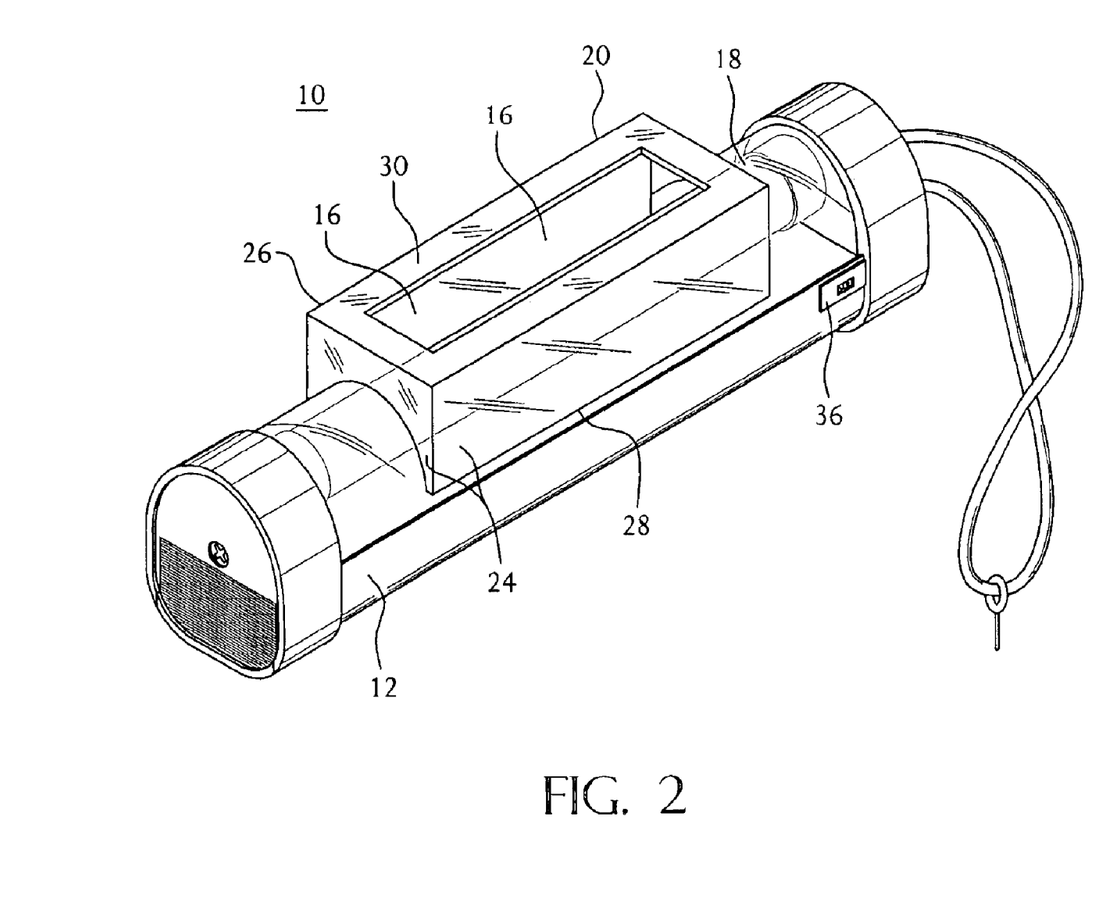
FIG. 2 is an oblique view of a germicidal UV lamp of the present invention.

FIG. 2 shows a germicidal lamp of the present invention based upon modifications to the lamp of FIG. 1. The lamp 10 of FIG. 2 has the cover section removed, and it is replaced by a UV light shield 20. The light shield 20 has an aperture 16, allowing light from the UV light source 18 to pass out of the shield. The light shield 20 may form the aperture by having side walls 24 with an upper edge 26 and a lower edge 28, and a top plate 30 provided at the upper edge 26 of the side walls having the aperture 16 formed therein. The aperture 16 may be formed to various sizes and shapes to allow UV light to pass from the UV light source 18. In a preferred embodiment, the light shield is formed from tinted translucent plastic that acts as a filter of UV radiation. In the preferred embodiment, the tint color is golden orange. This shield allows a user to observe when the UV light source 18 is illuminated, while shielding the user from harmful UV light. Alternatively, the light shield may be an opaque plastic or metal shield that is impenetrable to UV light. The light shield may be molded as a single piece.

As shown in FIGS. 2, 3a, 3b, and 3c, a switch cover 36 is formed on the housing 12. The switch cover 36 has an opening 38 which is sized to be sufficiently small to prevent a human child's finger, even of toddler size, from being inserted through the opening. Thus, a child would not be able to gain access to the switch.

Figure 3A:
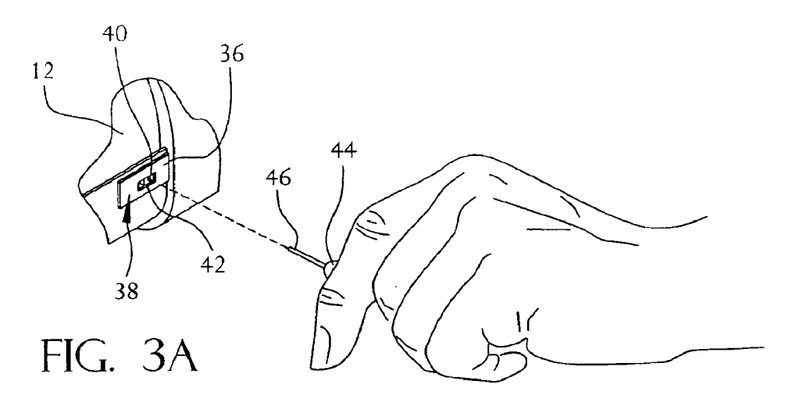
FIGS. 3a, 3b, and 3c show the operation of the safety switch.
Figures 3B, 3C:
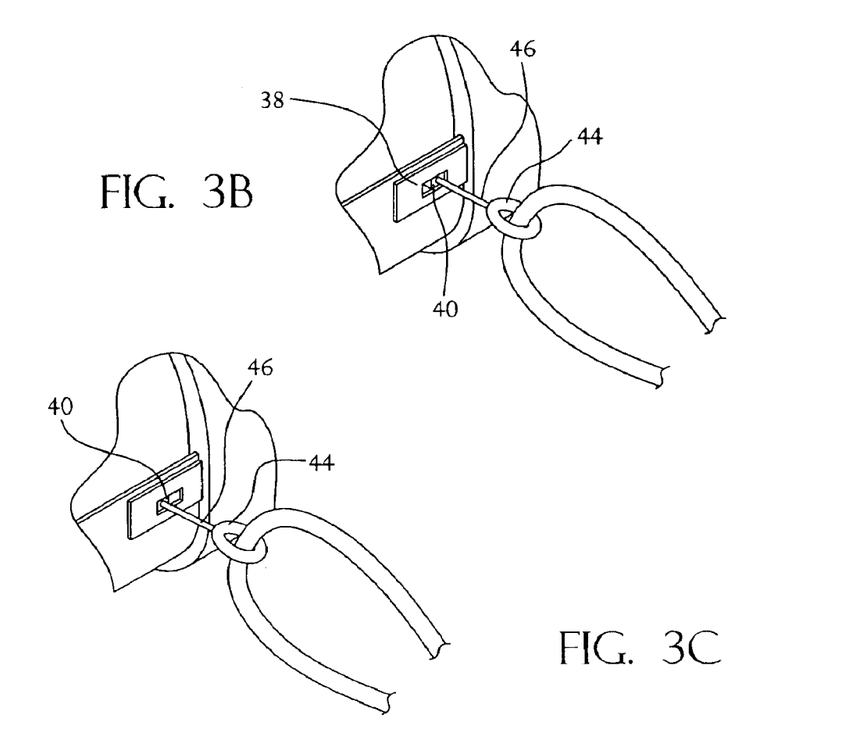

The safety switch 40 is located on the housing 12 beneath the switch cover 36. The switch 04 of the commercially available lamp in FIG. 1 may be modified to safety switch 40. The switch 40 is aligned with the switch cover and accessible through the opening 38 in the switch cover 36. The switch 40 has a tool engaging portion, in this embodiment a hole 42 adapted to engage with an activation tool 44. The activation tool 44 in this embodiment has a protrusion, specifically a pin 46, adapted to engage the hole 42 and operate the switch 40 between an on and an off position. The tool 44 may also have a ring eyelet so that it can be attached to a key chain or lanyard, or a finger tab (68, FIG. 4) with an eyelet. The pin 46 is inserted though the opening 38 in the switch cover 36 and mates with the hole 42. The switch 40 can then be moved from an off position (FIG. 3c) to an on position (FIG. 3b).

Figure 4A:
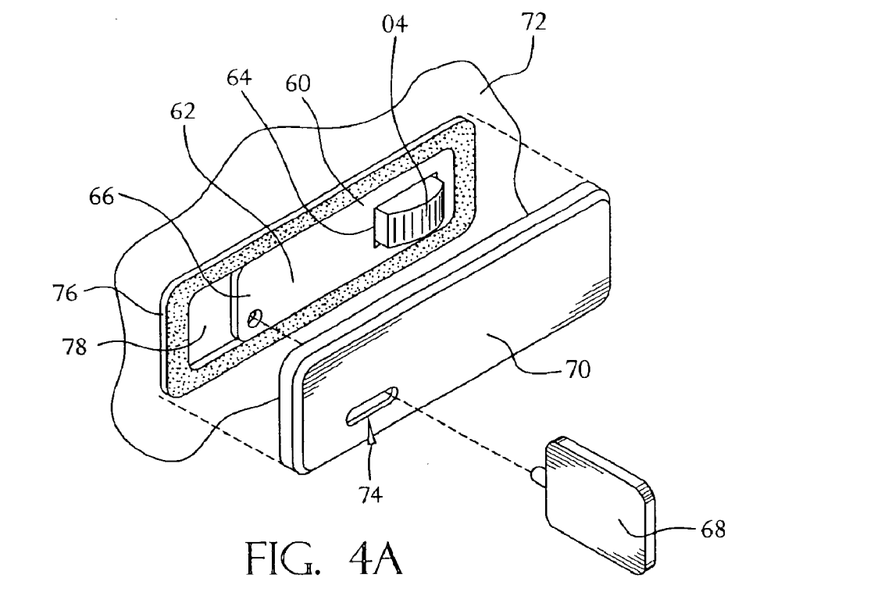
FIGS. 4a and 4b show an alternative embodiment of the safety switch.
Figure 4B:
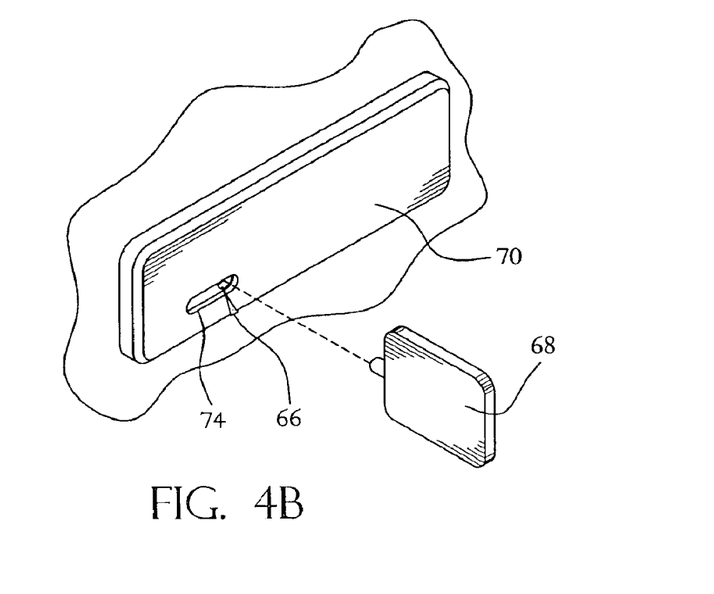

FIGS. 4a and 4b shows another embodiment whereby a standard switch on a commercial lamp may be converted into a safety switch 60 according to the present invention. A plate 62 is provided with a switch engaging cut-out 64 that engages the standard switch 04. The plate 62 has a tool-engaging portion, herein a hole 66 that is shaped to accept an activation tool 68, as described above. A cover 70 extends from the housing 72 over the switch 04 and the plate 62. The cover 70 has an opening 74 therein, which is aligned with the tool engaging portion 66. The slot 74 is large enough to allow the pin portion of the tool 68 to pass through. With the cover 70 installed, the switch 60 is no longer accessible by human fingers, but may be operated with the activation tool 68.

In the embodiment shown in FIGS. 4a and 4b, a back plate 76 is provided surrounding the plate and the switch and forming a channel 78 which limits the sliding movement of the plate 62. Alternately, the cover 70 may be formed with a channel on its inner surface.

Figure 5:
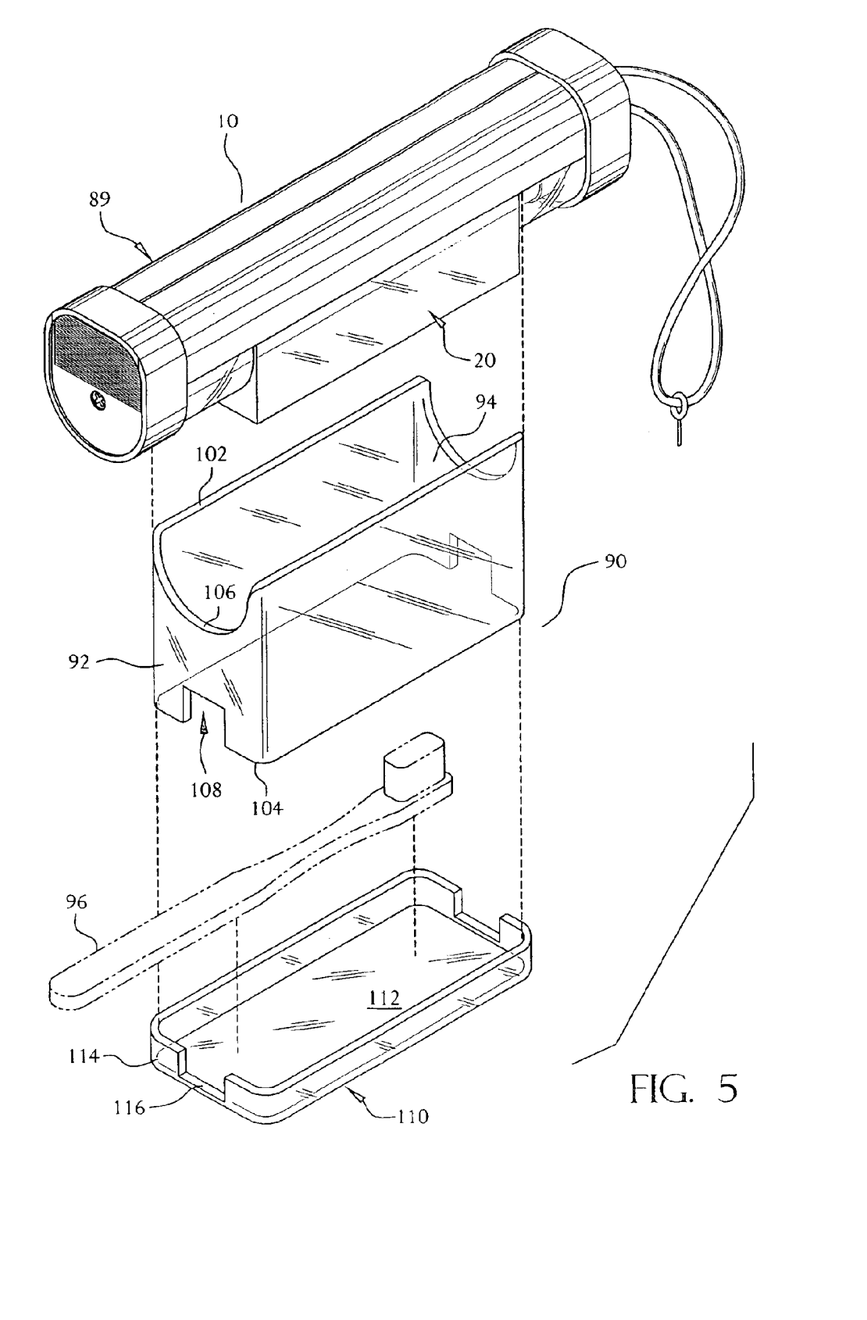
FIG. 5 shows an oblique exploded view of an embodiment of the lamp in combination with a degermination chamber.

It is appreciated that a user may want to routinely sterilize an object, such as a toothbrush, with the germicidal lamp. Thus, the germicidal lamp 10 of the present invention is further provided with a degermination chamber 90 as shown in FIG. 5. The degermination chamber 90 has side and end walls 92 which define a chamber 94 for receiving an object to be sterilized, such as a toothbrush 96. The walls 92 may be tinted UV absorbing plastic as described above in connection with the light shield 20. Alternatively, the walls may be an opaque plastic or metal that is impenetrable to UV light. The walls 92 have a first edge 102 to be positioned adjacent the housing, and a second edge 104 opposite the first edge 102.

As shown in FIG. 5, the degermination chamber 90 is adapted to surround the aperture of the light shield 20. A portion of the degermination chamber is adapted to conform to the shape of the housing as, in this embodiment, the end walls 92 are provided with saddle portions 106 at the top, such that the saddle portions conform to the shape of the ends of the light shield. The bottom edge 104 of each of the end walls can have indentations 108 at both ends adapted to receive the bristle end of a toothbrush, such that two toothbrushes brushes can be kept in the chamber. .

The degermination chamber also has a removable base 110. The base 110 has a floor plate 112 and side walls 114 extending from the floor plate 112. The side walls can be formed having indentations 116 adapted to receive objects for sterilization such as toothbrush 96. The base 110 may be tinted UV absorbing glass as described above in connection with the light shield 100. The side walls 114 of the base 110 are contoured to surround the bottom edge 104 of the degermination chamber 90.

Figure 6:
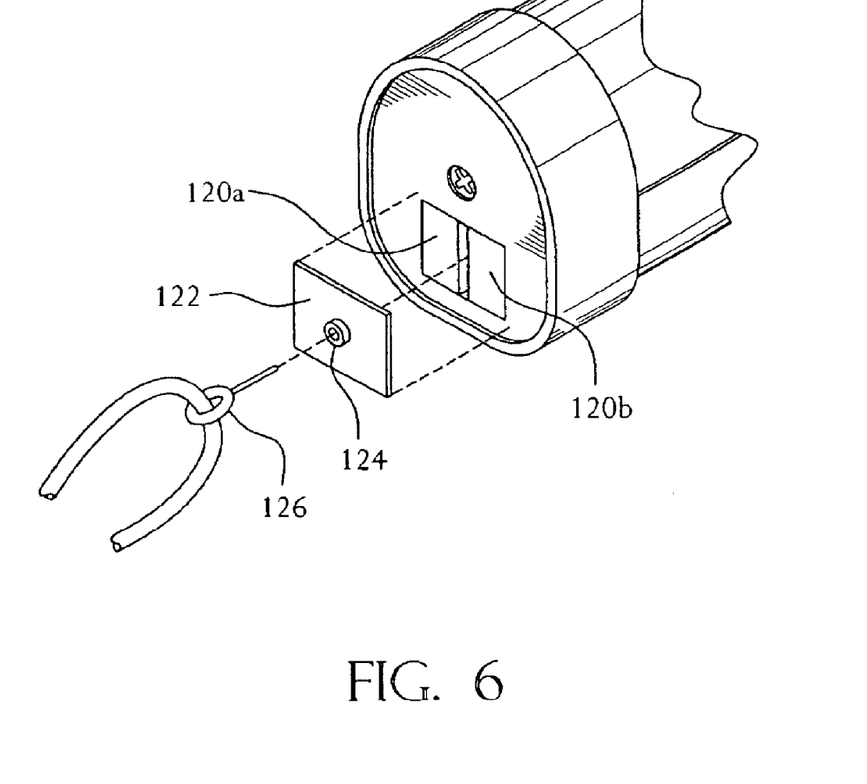
FIG. 6 shows an alternative safety switch in which a tool is used to make electrical contact between two electrical terminals.

FIG. 6 shows an embodiment with another safety feature. Electrical terminals 120(a) and 120(b) in series electrical communication with the power source and the UV lamp. The terminals 120(a) and (b) are in close proximity, but do not contact each other. A cover 122 is placed over the terminals 120(a) and 120(b) so that they are not exposed. The cover 122 has an opening 124 which is aligned with the space between the two terminals 120(a) and (b) and shaped to accept an activation tool 126. In this embodiment, the tool 126 is made of conductive material so that when the tool 126 is inserted into the opening 124, thereby contacting both terminals 120(a) and (b), current is able to flow between the terminals. The circuit comprised of the terminals 120(a) and (b), the power source and the UV light source is completed by inserting the tool 126 into the opening 124, and the UV light source is activated. The UV light source is turned off by removing the tool 126 from the opening 124. The cover 122 need not be removable; the end cap could be made in a single piece instead.

Figure 7A:
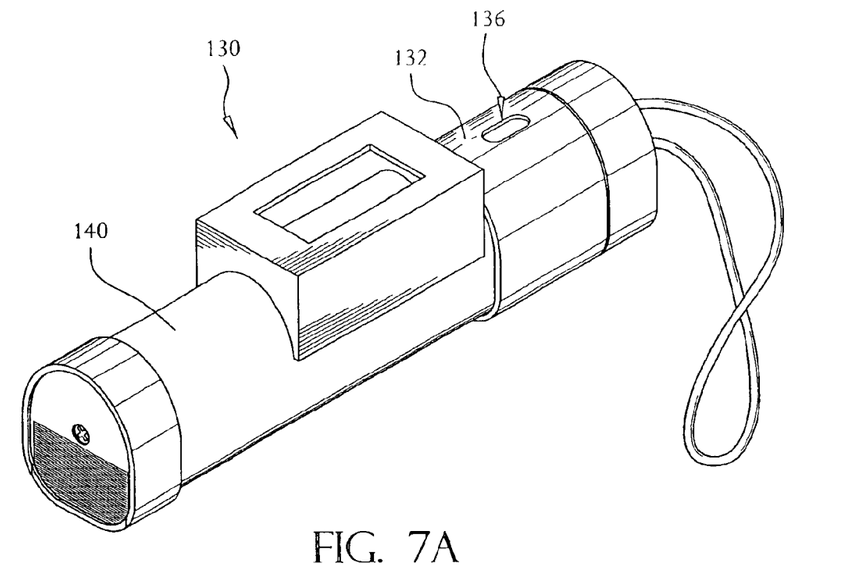
FIGS. 7a and 7b are oblique views of a germicidal lamp of the present invention having a moveable cover for preventing access to a switch.
Figure 7B:
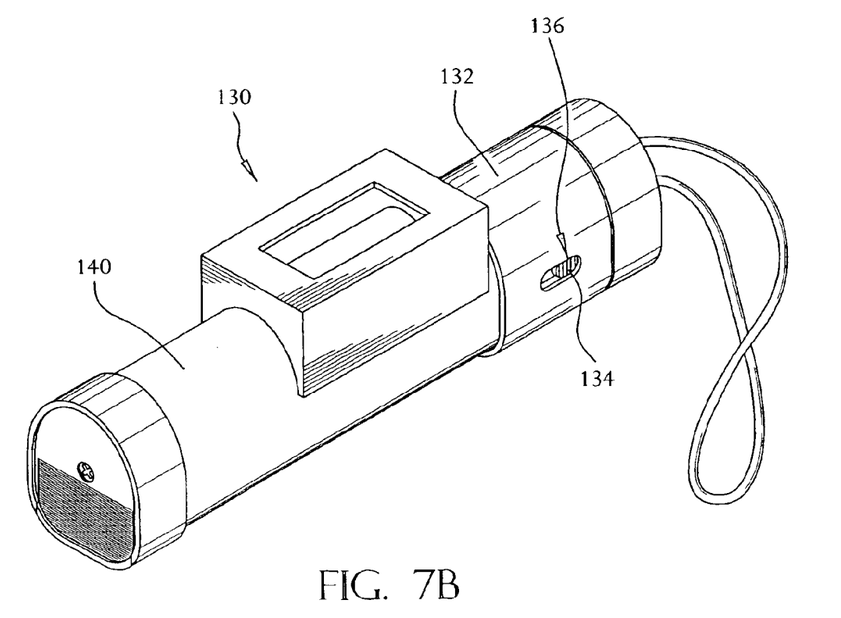

FIGS. 7a and 7b show another embodiment lamp 130 with a moveable safety cover 132 that selectively permits access to a switch 134. The cover 132 has a slot 136 therein and is movably connected to the housing 140, and can move circumferentially about the housing 140. The cover 132 may be moved between several positions. In the safe position, shown in FIG. 7a, the slot 136 is not aligned with the switch 134, so that the cover 132 prevents access to the switch 134. In the second position, shown in FIG. 7b, the slot 136 is aligned with the switch 134, so that access to the switch 134 is available through the slot 136. The switch 134 can also be formed as a safety switch which can only be activated with an activation tool, described in detail above.

Figure 8A:
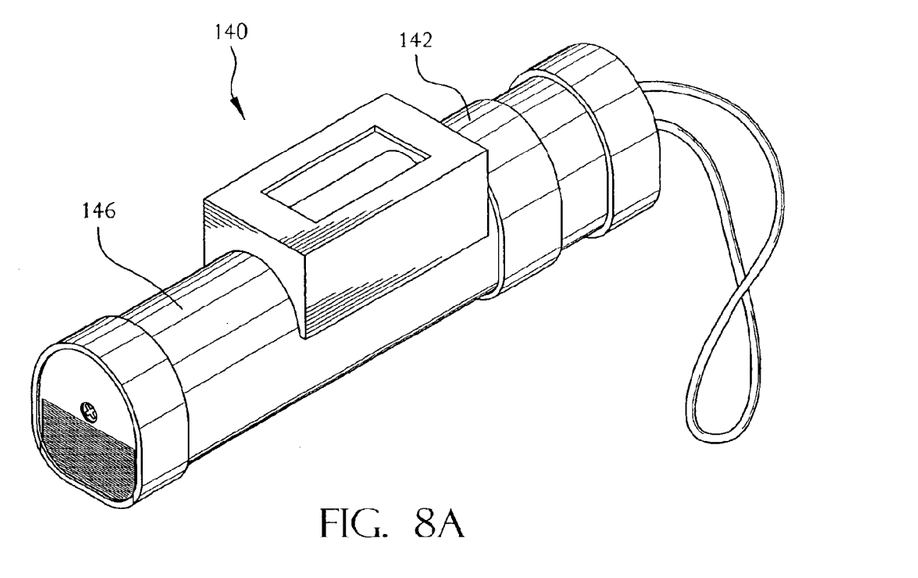
FIGS. 8a and 8b are oblique views another embodiment of a germicidal lamp of the present invention having a moveable cover for preventing access to a switch.
Figure 8B:
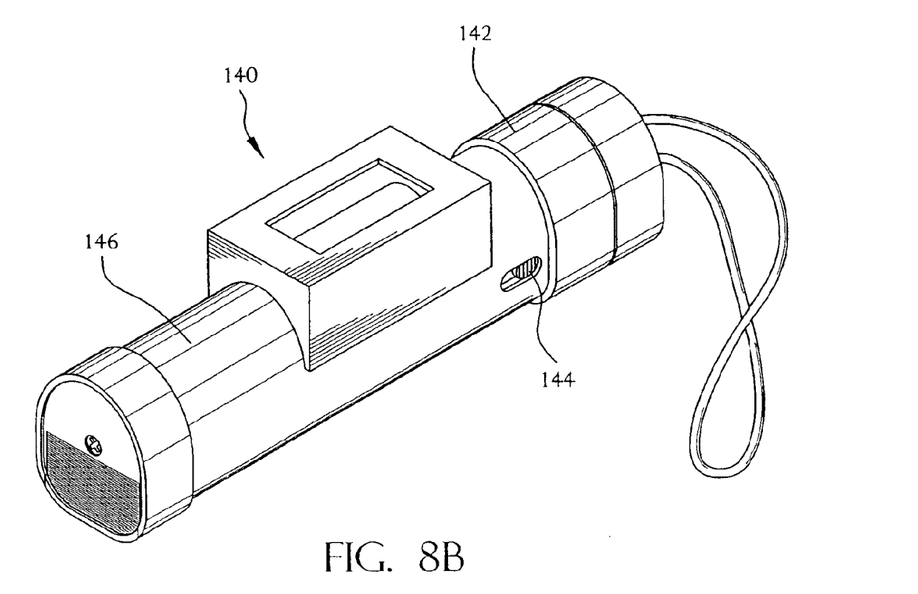

FIGS. 8a and 8b show another embodiment of the lamp 140 with a moveable safety cover 142 which selectively permits access to the switch 144. The cover 142 and is movably connected to the housing 146, and is adapted to move longitudinally along the housing 146. In this embodiment, the slot is not required, and the cover 142 is moved from a position which covers the switch 144, as shown in FIG. 8a, to a position which does not cover the switch 144, as shown in FIG. 8b.

Figure 9:
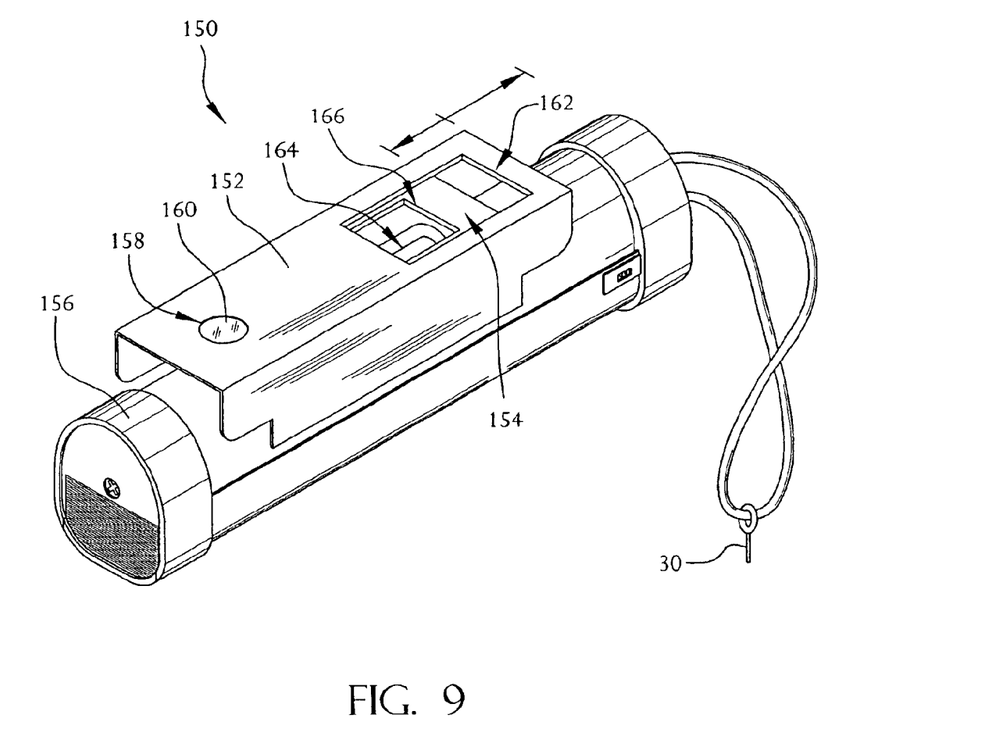
FIG. 9 is an oblique view of a germicidal lamp incorporating a moveable guard plate.

FIG. 9 shows a UV lamp 150 with a guard plate 152 attached. The guard plate 152 is shown attached to the light shield 154, although it may also be attached to the housing 156 if no light shield is present. The guard plate 152 has a first opening 158 with a filter 160 disposed therein. The filter 160 prevents transmission of UV light, while permitting transmission of visible light. The guard plate 152 has a second opening 162 that allows all light from the UV light source to pass through. The guard plate 152 is movably attached, and is movable between a first position and a second position.

In the first position, the first opening 158 covers the aperture 164 of the UV lamp, and if a light shield 154 is present, the light shield opening 166. In the first position, substantially all UV light is blocked by the filter 160, while visible light is transmitted through the first opening 158, so that the user may visibly inspect whether the light source is turned on. In the second position, the area of the guard plate 152 having the second opening 162 is aligned with the aperture 164 and light shield opening 166. In the second position, UV light is transmitted through the second opening 162. The user can move the guard plate 152 to the second position to permit UV light to radiate from the device.

Figure 10:
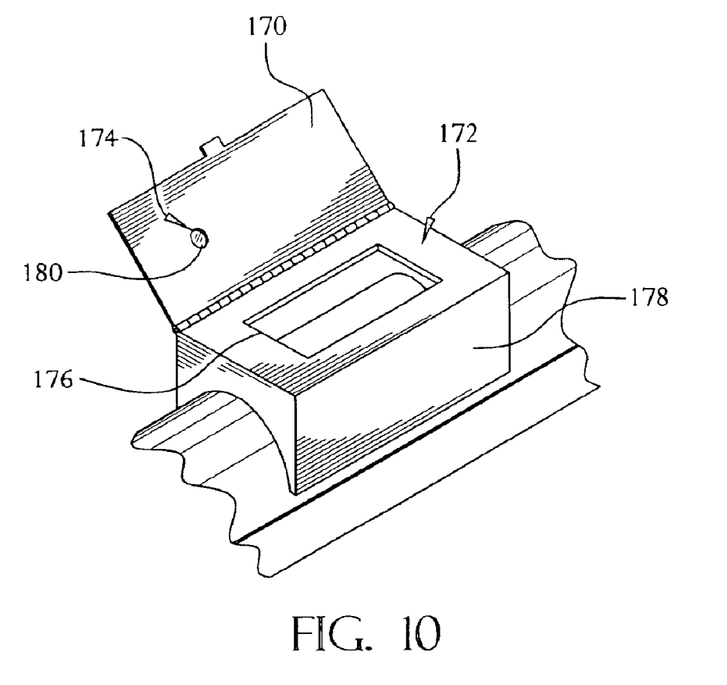
FIG. 10 shows an alternative embodiment of the guard plate.
Figure 11:
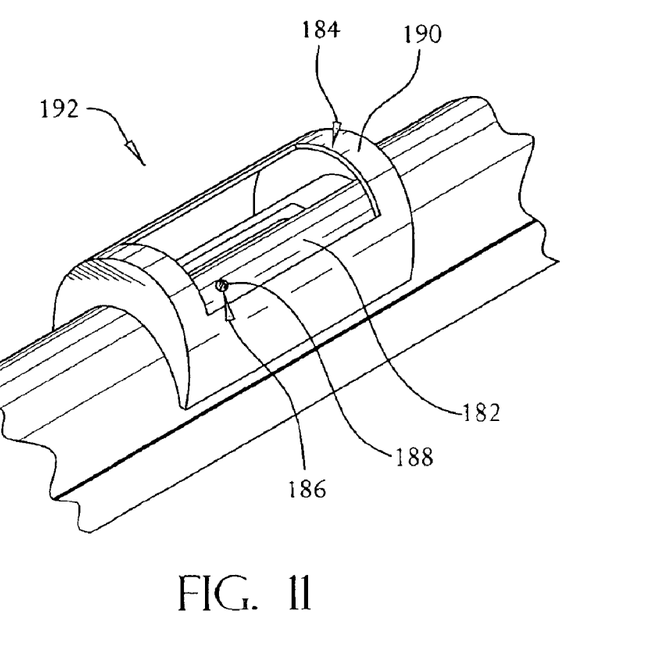
FIG. 11 shows a third embodiment of the guard plate.

FIGS. 10 and 11 show alternative embodiments of a germicidal lamp incorporating a guard plate. In FIG. 10, a guard plate 170 is rotatably attached to the light shield 178 top plate 172. The guard plate 170 has an opening 174 which is aligned with the light shield opening 176 when the guard plate 170 is closed against the light shield top plate 172. The single opening 174 has a filter 180 disposed therein which prevents transmission of substantially all UV light, but transmits visible light. The user rotates the guard plate 170 to an open position in order to allow UV light to radiate from the lamp.

FIG. 11 shows the guard plate 182 as a sliding shutter that slides to enclose a light shield 190 opening 184. The guard plate 182 has an opening 186 with a filter 188 therein which blocks UV light while transmitting visible light. The guard plate 182 may be slid to cover the entire light shield opening 184, preventing UV light from exiting the lamp 192, but allowing visible inspection of the light source via the filter 188 to determine if the UV light source is powered on. The guard plate 182 may then be moved to a position allowing UV light to exit the lamp 192 through the light shield opening 184.

Figure 12:
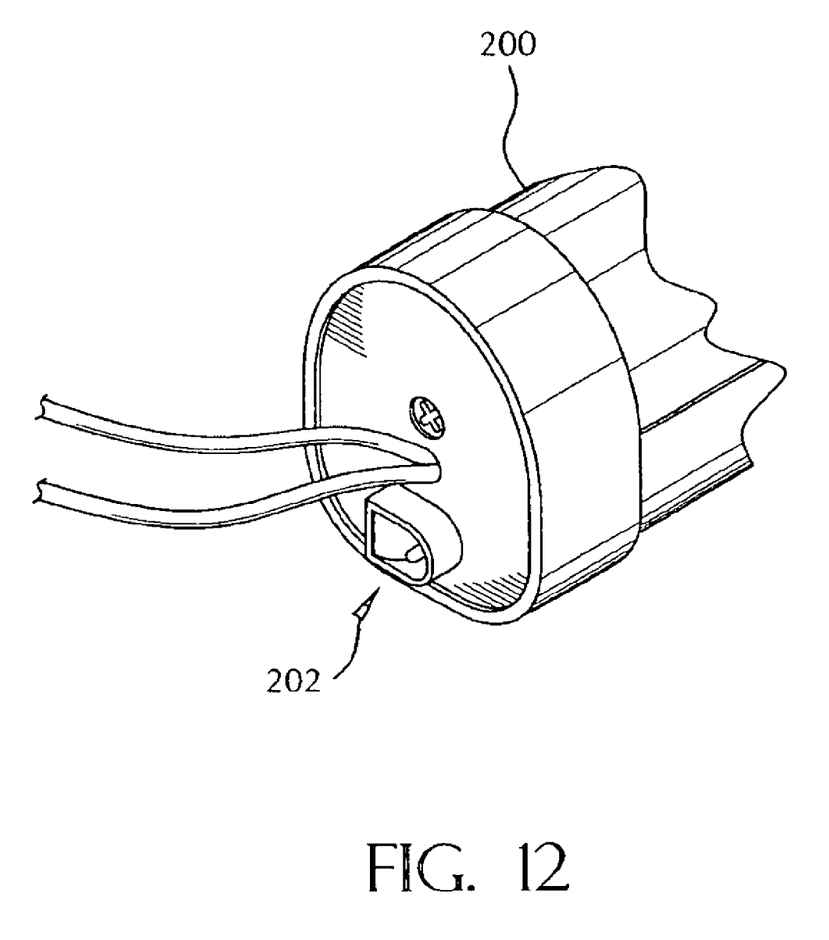
FIG. 12 is an oblique view of an embodiment with an AC/DC power adapter connector.

FIG. 12 shows an embodiment of the germicidal lamp 200 with a connector socket 202 to receive the plug of a standard AC/DC adapter. The connector makes operation of the lamp possible using an external power source, or recharging the lamp's internal batteries. When the lamp is powered from the adapter, the current is routed to continue the safety protections of the various embodiments of switches described above.

The present invention may be embodied in other specific forms without departing from the spirit or essential attributes thereof and, accordingly, reference should be made to the appended claims, rather than to the foregoing specification, as indicating the scope of the invention.

What is claimed is:

1. A germicidal UV lamp, comprising:
   a. a housing, the housing having a UV light source therein and having at least one aperture allowing the passage of UV light out of the housing;
   b. a safety switch on the housing for activating the light source, the safety switch having a tool engaging portion adapted to engage an activation tool;
   c. a means for physically obstructing finger access to the safety switch; and,
   d. an activation tool adapted to engage the tool engaging portion of the safety switch in order to selectively non-rotatably translate the safety switch between an on and an off position.

2. The germicidal UV lamp according to claim 1, wherein the means far physically obstructing finger access to the safety switch comprises a switch cover formed on the housing, the switch cover having an opening therein adapted to allow passage of the activation tool, the opening being sufficiently small to prevent a human finger from being inserted in the opening.

3. The germicidal UV lamp according to claim 1, wherein the activation tool has a protrusion and the tool engaging portion is an opening adapted to receive the protrusion.

4. The germicidal UV lamp according to claim 1, further comprising a light shield extending from the housing, the light shield surrounding the aperture.

5. The germicidal UV lamp according to claim 4, wherein the light shield has side walls with an upper edge, the upper edge of the side walls defining the aperture.

6. The germicidal UV lamp according to claim 4, wherein the light shield is formed from a tinted translucent plastic material which absorbs UV light.

7. A germicidal UV lamp and degermination chamber comprising:
   a. a lamp housing, the housing having a UV light source therein and having at least one aperture allowing the passage of UV light out of the housing; and
   b. a degermination chamber having an opening, the opening being sized and shaped to allow the degermination chamber to be connected to an exterior of the lamp housing adjacent the aperture and comprising a wall with a slot therein for receiving objects to be sterilized by UV light from the aperture.

8. The germicidal UV lamp and chamber according to claim 7, wherein the chamber includes means for opening the chamber to place therein an object to be sterilized.

9. The germicidal UV lamp and chamber according to claim 7, wherein the degermination chamber is formed from material which blocks the transmission of UV light.

10. The germicidal UV lamp and chamber according to claim 7, wherein the degermination chamber is formed from a translucent material that absorbs UV light.

11. A germicidal UV lamp, comprising:
   a. a housing, the housing having a UV light source therein and at least one aperture allowing the passage of UV light;
   b. a switch formed on the housing, the switch in electrical communication with a power source; and,
   c. a cover mounted to the housing for sliding movement relative to the housing and selectively moveable in relation to the switch and the housing for preventing finger access to the switch when the cover is moved to a first position to cover the switch and allowing finger access to the switch when the cover is moved to a second position to uncover the switch.

12. A germicidal UV lamp, comprising:
   a. a housing having a UV light source therein and having, at least one aperture allowing the passage of UV light;
   b. opposing electrical terminals located on the housing, separated by a gap, and in electrical communication with a power source;
   c. a cover over the terminals, the cover preventing finger access to the terminals, the cover having an opening therein adapted to allow passage of an activation tool; and d. an activation tool, the activation tool formed from an electrically conductive material, the activation tool adapted to pass through the opening in the cover, and being sized and shaped to bridge the gap to bring the opposing terminals into electrical communication, wherein upon insertion into the gap, the activation tool contacts each terminal thereby completing a circuit and allowing current to flow through the terminals and the activation tool.

13. The germicidal UV lamp according to claim 12, further comprising a light shield extending from the housing and surrounding the aperture.

14. The germicidal UV lamp according to claim 12, further comprising a degermination chamber for receiving objects to be sterilized by the UV lamp, a portion of the chamber being adapted to conform to the shape of the housing.

15. A germicidal UV lamp, comprising:
 a. a housing having a UV light source therein and at least one aperture allowing the passage of UV light from the housing;
 b. a switch on the housing, the switch in electrical communication with a power source;
 c. a plate having an opening forming a switch engaging portion, the switch engaging portion operatively engaging the switch to non-rotatably translate the switch between an on position and an off position, and the plate having a tool engaging portion shaped to engage an activation tool;
 d. a switch cover, the switch cover covering the switch and plate, the switch cover having an opening therein adapted to allow the passage of an activation tool; and,
 e. an activation tool adapted to pass through the opening in the switch cover, the activation tool adapted to engage the tool engaging portion of the plate to selectively move the plate to in turn non-rotatably translate the switch between the on and off positions.

16. The germicidal UV lamp according to claim 15, further comprising a back plate connected to the housing, the back plate surrounding the plate and the switch, the back plate forming a channel which constrains motion of the plate.

17. The germicidal UV lamp according to claim 15, wherein the switch cover has an inner surface adjacent the plate and the switch, the switch cover having a channel formed on its inner surface which constrains movement of the plate.

18. A germicidal UV lamp comprising:
 a housing having a UV light source therein and at least one aperture allowing the passage of UV light; and
 a degermination chamber having an opening, the opening being sized and shaped to allow the degermination chamber to be connected to an exterior of the housing adjacent the aperture and comprising UV absorbing translucent material, the chamber being open to the aperture for receiving UV light.

19. The germicidal UV lamp of claim 18 further comprising a light shield extending from the housing, the light shield having a window permitting the transmission of UV light from the housing into the degermination chamber, the degermination chamber being adapted to conform to the shape of the light shield.

20. The germicidal UV lamp of claim 18 wherein the UV absorbing translucent material is tinted.

21. The germicidal UV lamp of claim 1, further comprising blocking means moveably attached to the housing for selectively blocking the transmission of UV light from the housing, the blocking means comprising an opening, the opening having a filter therein, the filter adapted to block the transmission of UV light while allowing passage of visible light, the opening being alignable with the window.

22. The germicidal UV lamp and chamber of claim 7, further comprising blocking means moveably attached to the housing for selectively blocking the transmission of UV light from the lamp housing, the blocking means comprising an opening, the opening having a filter therein, the filter adapted to block the transmission of UV light while allowing passage of visible light, the opening being alignable with the window.

23. The germicidal UV lamp of claim 11, further comprising blocking means movably attached to the housing for selectively blocking the transmission of UV light from the housing, the blocking means comprising an opening, the opening having a filter therein, the filter adapted to block the transmission of UV light while allowing passage of visible light, the opening being alignable with the window.

24. The germicidal UV lamp of claim 12, further comprising blocking means movably attached to the housing for selectively blocking the transmission of UV light from the housing, the blocking means comprising an opening, the opening having a filter therein, the filter adapted to block the transmission of UV light while allowing passage of visible light, the opening being alignable with the window.

* * * * *